United States Patent
Maddi et al.

(10) Patent No.: US 12,055,505 B2
(45) Date of Patent: Aug. 6, 2024

(54) THERMO-PIEZORESISTIVE EMBEDDED WIRELESS SENSOR WITH REAL-TIME CONCRETE MONITORING

(71) Applicant: Sensytec, Inc., Houston, TX (US)

(72) Inventors: Sai Anudeep Reddy Maddi, Houston, TX (US); Derman Smith Santander Amador, Houston, TX (US); Ody Roy La Paz Guerra, Houston, TX (US)

(73) Assignee: Sensytec, Inc., Houston, TX (US)

( * ) Notice: Subject to any disclaimer, the term of this patent is extended or adjusted under 35 U.S.C. 154(b) by 0 days.

(21) Appl. No.: 18/171,767

(22) Filed: Feb. 21, 2023

(65) Prior Publication Data

US 2023/0194453 A1    Jun. 22, 2023

Related U.S. Application Data

(63) Continuation of application No. 17/380,115, filed on Jul. 20, 2021, now Pat. No. 11,614,420.

(Continued)

(51) Int. Cl.
*G01N 33/38* (2006.01)
*G01N 27/04* (2006.01)

(52) U.S. Cl.
CPC ......... *G01N 27/046* (2013.01); *G01N 33/383* (2013.01)

(58) Field of Classification Search
CPC ...... G01N 27/04; G01N 27/02; G01N 27/021; G01N 27/048
See application file for complete search history.

(56) References Cited

U.S. PATENT DOCUMENTS

| 10,481,143 B2 | 11/2019 | Vipulanandan |
| 2007/0019506 A1 * | 1/2007 | Mandal ................. G01N 29/11 381/113 |

(Continued)

FOREIGN PATENT DOCUMENTS

| CA | 2681452 A1 * | 4/2010 | ............ G01N 17/04 |
| WO | 2017011460 A1 | 1/2017 | |

OTHER PUBLICATIONS

International Search Report for International Application No. PCT/US2021/042299 mailed Oct. 22, 2021.

(Continued)

*Primary Examiner* — Manish S Shah
*Assistant Examiner* — Sharad Timilsina
(74) *Attorney, Agent, or Firm* — Perilla Knox & Hildebrandt LLP; Stephanie L. Davy-Jow

(57) ABSTRACT

Embodiments are described herein for a sensor device created for determining and monitoring quality and strength developments in concrete and other materials using temperature and electrical resistivity parameters. The embodiments described herein may be utilized in the construction industry for real-time monitoring of concrete and cement structures or for monitoring the strength and quality of soils, polymers, and liquid additives as well. According to various embodiments, alternating current (AC) electrical and temperature measurements may be performed to correlate to the quality and performance of the concrete, polymers, treated soils, and other materials. These measurements may be made by compact sensor devices that are configured to read both temperature and AC electrical measurements continuously to quantify the performance of materials.

18 Claims, 13 Drawing Sheets

Related U.S. Application Data

(60) Provisional application No. 63/054,283, filed on Jul. 21, 2020.

(56) References Cited

U.S. PATENT DOCUMENTS

| | | | |
|---|---|---|---|
| 2014/0008756 A1 | 1/2014 | Pei et al. | |
| 2015/0240627 A1* | 8/2015 | Gao | E21B 47/13 |
| | | | 324/700 |
| 2017/0160111 A1* | 6/2017 | Dowdall | G01N 33/383 |
| 2017/0238073 A1* | 8/2017 | Wittler | H04W 4/70 |
| | | | 340/870.09 |
| 2018/0238820 A1* | 8/2018 | Ghods | G01N 27/026 |

OTHER PUBLICATIONS

Written Opinion for International Application No. PCT/US2021/042299 mailed Oct. 22, 2021.

* cited by examiner

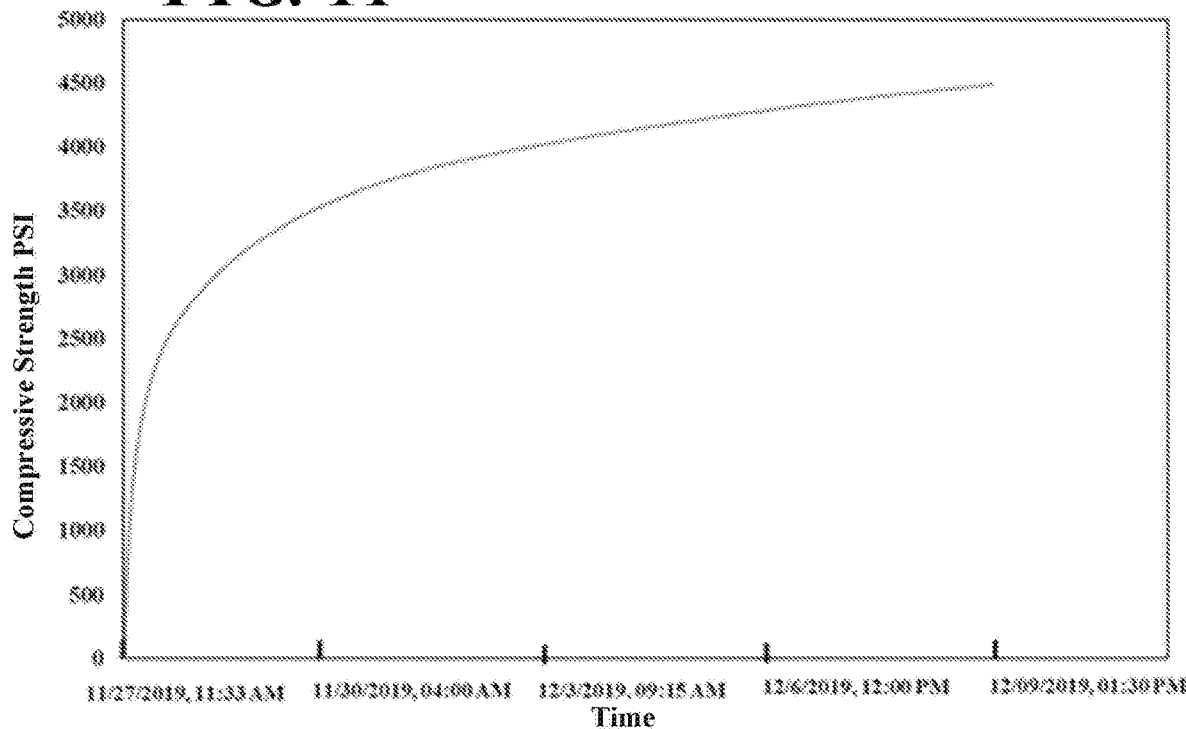
FIG. 11 Compressive Strength using Temperature, PSI
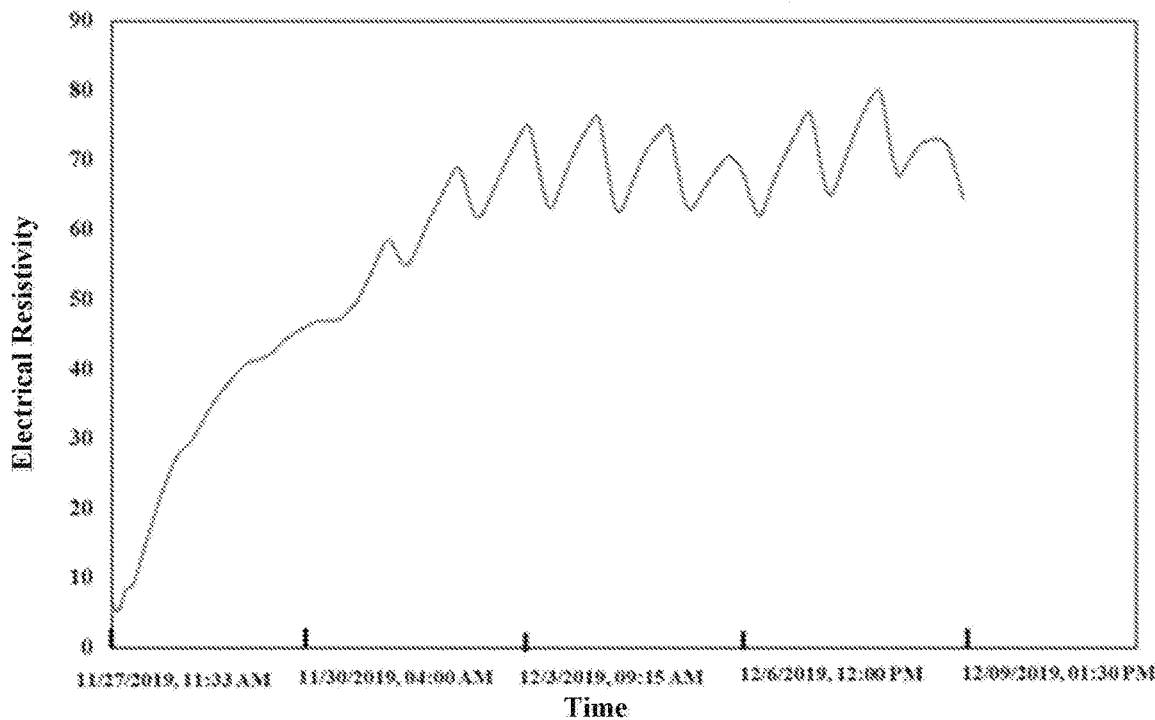
FIG. 12 Electrical Resistivity

| Cumulative Resistivity Time Factor (RTF) | Strength, Mpa |
|---|---|
| 51.7 | 9.1 |
| 354.8 | 17.2 |
| 1061.8 | 21.0 |

THERMO-PIEZORESISTIVE EMBEDDED WIRELESS SENSOR WITH REAL-TIME CONCRETE MONITORING

CROSS-REFERENCE TO RELATED APPLICATION

This application is a continuation of U.S. patent application Ser. No. 17/380,115 filed Jul. 21, 2021, entitled "THERMO-PIEZORESISTIVE EMBEDDED WIRELESS SENSOR WITH REAL-TIME CONCRETE MONITORING," which claims the benefit of and priority to U.S. Provisional Patent Application No. 63/054,283 filed Jul. 21, 2020, entitled "THERMO-PIEZORESISTIVE EMBEDDED WIRELESS SENSOR WITH REAL-TIME CONCRETE MONITORING," the contents of which being incorporated by reference in their entirety herein.

BACKGROUND

Cement and concrete are used worldwide in a variety of construction projects, from small to large residential homes to even massive commercial structures. Because of this large consumption of concrete, new techniques and methods of quality control have arisen. Concrete is a unique building material that can withstand both fire and water, among others. Because of this unique quality, it is the most widely used building material in the world. Additionally, concrete is one of the oldest known man-made materials and currently about ten billion tons of concrete are produced every year.

Due to the rapid development of more demanding concrete infrastructures worldwide, a variety of concrete types are currently available which include high strength concrete, high density concrete, high sulphate resistant concrete, lightweight concrete, quick setting concrete, and so on. These different variations in concrete are achieved by mix of various admixtures, changing aggregates, water to cement ratios, and other parameters. Admixtures are also used to modify the hydration process of concrete to slow down or speed up the hydration process. Some admixtures are added into the concrete mixtures to obtain higher compressive strength, durability, and/or to improve the workability. Due to such high variation in requirements, it is important to monitor the strength and quality of concrete continuously. Real-time monitoring for concrete is a revolutionary approach because it allows the end user to make more quick and informed decisions during and after the placement of the concrete.

Structures rely on concrete as a construction agent due to its compressive strength, durability, and cost efficiency. Concrete is a heterogeneous material that consist of a mixture of water, cement, fine aggregates, coarse aggregates, fiber/steel, and different other admixtures which makes it very sensitive during the curing process. During this process, concrete gains close to 90-95% of its compressive strength in twenty-eight days of curing and about 3-5% increase when cured up to six months.

Concrete is believed to gain strength over time even after six months, but it is crucial to quantify and monitor the strength of concrete during and after the 28 days period, as it reaches close to 90 to 95% strength. There are several techniques used to monitor the curing process of fresh concrete nowadays, but without accurate and continuous monitoring, these techniques are not enough for attaining real-time data on concrete strength developments. Thus, concrete needs to be monitored precisely from right after it is poured until the twenty-eighth day to determine whether it has achieved the specified design strength. For any concrete mix, it is necessary to monitor the strength development at an early age because changes in the environment such as temperature and cold weather can affect the curing process of fresh concrete. The main purpose of quality control methods is to prevent catastrophes and preserve human lives, ensure best construction practices, and expedite the construction processes while cutting costs.

BRIEF SUMMARY OF THE INVENTION

Embodiments are described herein for a wireless sensor created for recording, monitoring, and characterizing quality and strength developments in concrete using temperature and electrical methods. In some embodiments, the concrete is "fresh concrete," or, in other words, recently-poured concrete. The embodiments described herein may be utilized in the construction industry for real-time monitoring of concrete and other cementitious materials for continuous characterization. The embodiments described herein may also be utilized for monitoring the strength and quality of soils, polymers, solutions, and liquid additives as well. In accordance with an embodiment of the invention, a method is described that comprises performing electrical impedance measurements inside concrete in real time for both wet and hardened conditions in laboratory and field applications. According to various embodiments, alternating current (AC) electrical and temperature measurements may be performed to correlate to the quality and performance of the concrete, polymers, treated soils, solutions, and other cementitious materials. These measurements may be made by compact wireless sensors configured to read both temperature and AC electrical measurements continuously to quantify the performance of materials.

In accordance with an embodiment of the invention, a method is provided for AC electrical impedance measurement inside cementitious materials and determining at least one characteristic of concrete, where temperature and/or geometrical factor correction are employed. Determining the characteristic of concrete may include, for example, at least one of the following: determining quality control parameters, such as water cement ratio, contaminations, setting times, and temperature; determining pore solution properties, such as electrical conductivity, transport properties, such as permeability, porosity, and diffusivity; determining durability characteristics, such as voids, cracking, corrosion, or any damage to the materials; determining performance characteristics, such as compressive strength and slump.

In accordance with embodiment of the invention, a method is provided comprising performing temperature and/or electrical impedance measurements in wet and/or solid (or hardened) cementious materials in laboratory and/or field settings in real time; transmitting the temperature and impedance measurements to a remote computing device (e.g., a server) for processing characteristics of cementitious materials; and communicating the characteristics of cementitious materials to a computing device associated with an enterprise. In accordance with an embodiment of the invention, a method for reuse of sensor with replaceable probe component is described.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Further characteristics, features, and benefits of the embodiments described herein will become evident after the clarification of the detailed illustration of figures.

FIG. 11 is a compressive strength plot showing compressive strength of concrete versus time according to various embodiments of the present disclosure.

FIG. 12 is an electrical resistivity plot showing electrical resistivity versus time according to various embodiments of the present disclosure.

DETAILED DESCRIPTION

Figure 1:
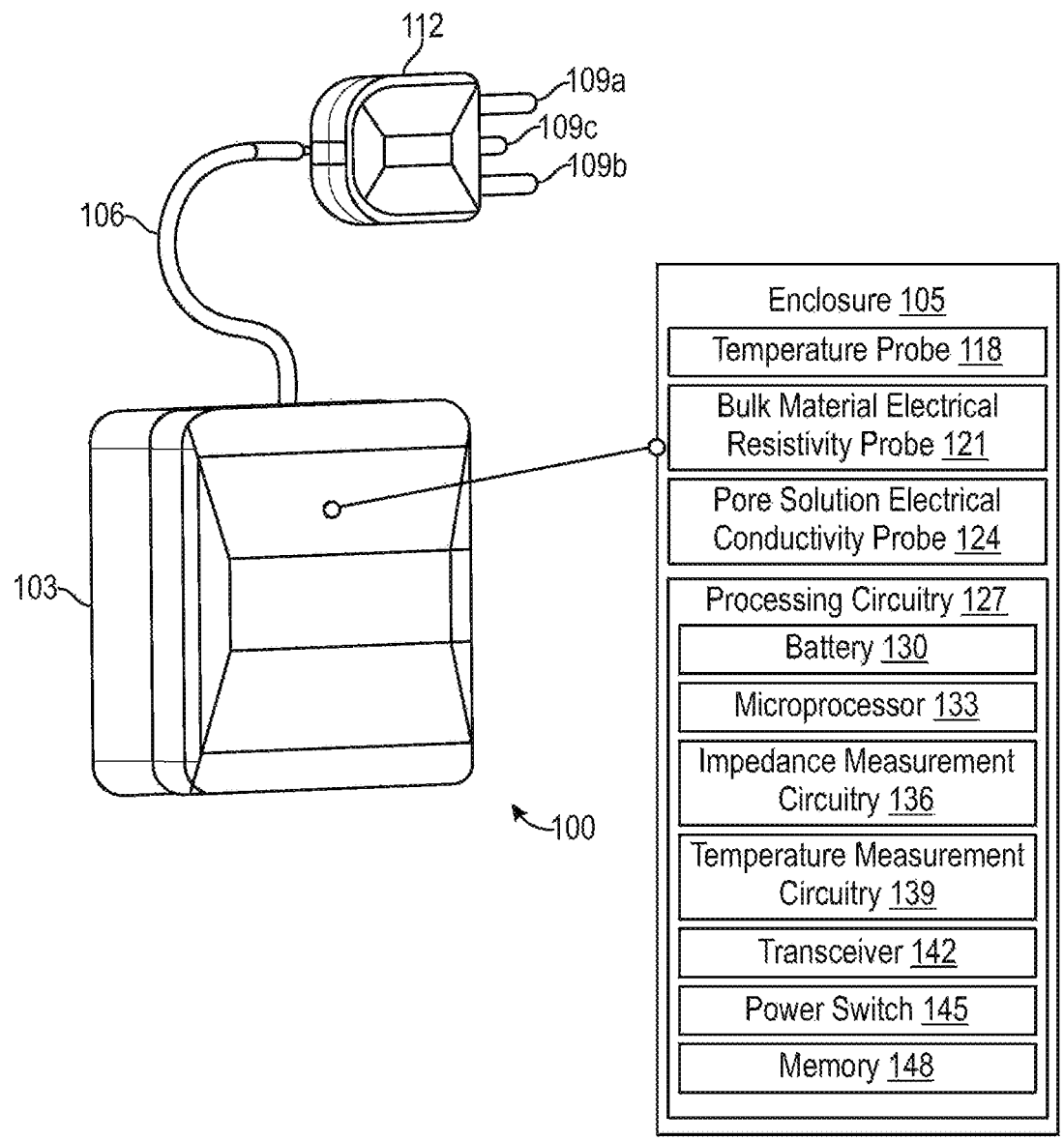
FIG. 1 is a perspective view of a sensor device for real-time concrete monitoring according to various embodiments of the present disclosure.

The present disclosure relates to a thermo-piezoresistive embedded wireless sensor with real-time concrete monitoring. Concrete material testing methods currently require concrete samples or "cylinders" to be collected from job sites for each of the concrete mix-designs used in a project. The samples are then carefully transported to a Materials Testing Lab (MTL) for testing. Typically, the MTL lets each concrete cylinder "specimen" cure for about three, seven, fourteen, or twenty-eight days before performing testing. Sequentially, after each concrete specimen is fully cured, the MTL performs a compressive strength test which includes performing various measurements by breaking each concrete cylinder in a compression-testing machine to determine at what pound-force per square inch (PSI) each concrete cylinder breaks. This assumes that the sample has not be broken during collection and/or transport.

The test results are sent to construction owners to inform the owners of the PSI of each concrete specimen, which is correlated to the PSI for concrete poured in the field. However, these testing methods have been around for decades and they do not provide the necessary information in real-time for construction owners, general contractors, suppliers, regulators, architects, and civil engineers to make quick and more informed decisions about the performance and quality of concrete. Currently, the seven days lead time that MTL takes before sending results back to the end user is a hurdle to the construction industry where time is money.

Establishing rapid real-time testing of concrete quality and strength is the current aspect of interest. The use of thermocouples and sensors for temperature measurement in concrete to predict the strength are also accepted in the building standards for construction. Nonetheless, temperature measurements have proved to be accurate in controlled environment settings, but there are several limitations in applying the technology to the field. One limitation is the temperature being influenced by the outside environment elements, such as hot and cold weather. Another limitation is that temperature measurements are affected by the size and thickness of the structure being built, and the location where a sensor is placed may affect readings due to a temperature of concrete varying from place to place. Notably, temperature sensors cannot differentiate between void space and the presence of concrete at the measurement location.

Furthermore, temperature measurements are not used solely for early concrete strength predictions due to temperature not being a true material property of concrete. On the other hand, electrical resistivity of concrete is a material property and provides accurate correlation to hydration reaction of concrete. This parameter can be used to predict a much more accurate strength predictions in fresh concrete. Estimation of strength and quality of concrete in real time using alternating current electrical resistivity measurements are described herein may provide contractors, owners, and others with highly accurate results, thereby reducing the dependence on break tests that are currently done, which cause longer construction waiting time and are expensive.

More details and features of the embodiments described herein will be described below. Specifically, the embodiments described herein address limitations within the current testing methods for concrete, cement, treated soils, solutions and polymers more particularly electrical methods and systems. Further, the embodiments described herein may utilize electrical impedance measurements to monitor the chemical reaction in concrete, such as fresh concrete, to determine the strength and quality thereof in real-time. The alternating current electrical impedance measurement may be performed at high-frequencies and may be used to calculate electrical resistivity based on a correction to geometric factor K—temperature adjustment. The embodiments described herein may provide electrical conductivity of pore solution inside cementitious materials in real time.

Other aspects and features of the present invention will become apparent to those ordinarily skilled in the art upon review of the following description of specific embodiments of the invention in conjunction with the accompanying figures.

Figure 2:
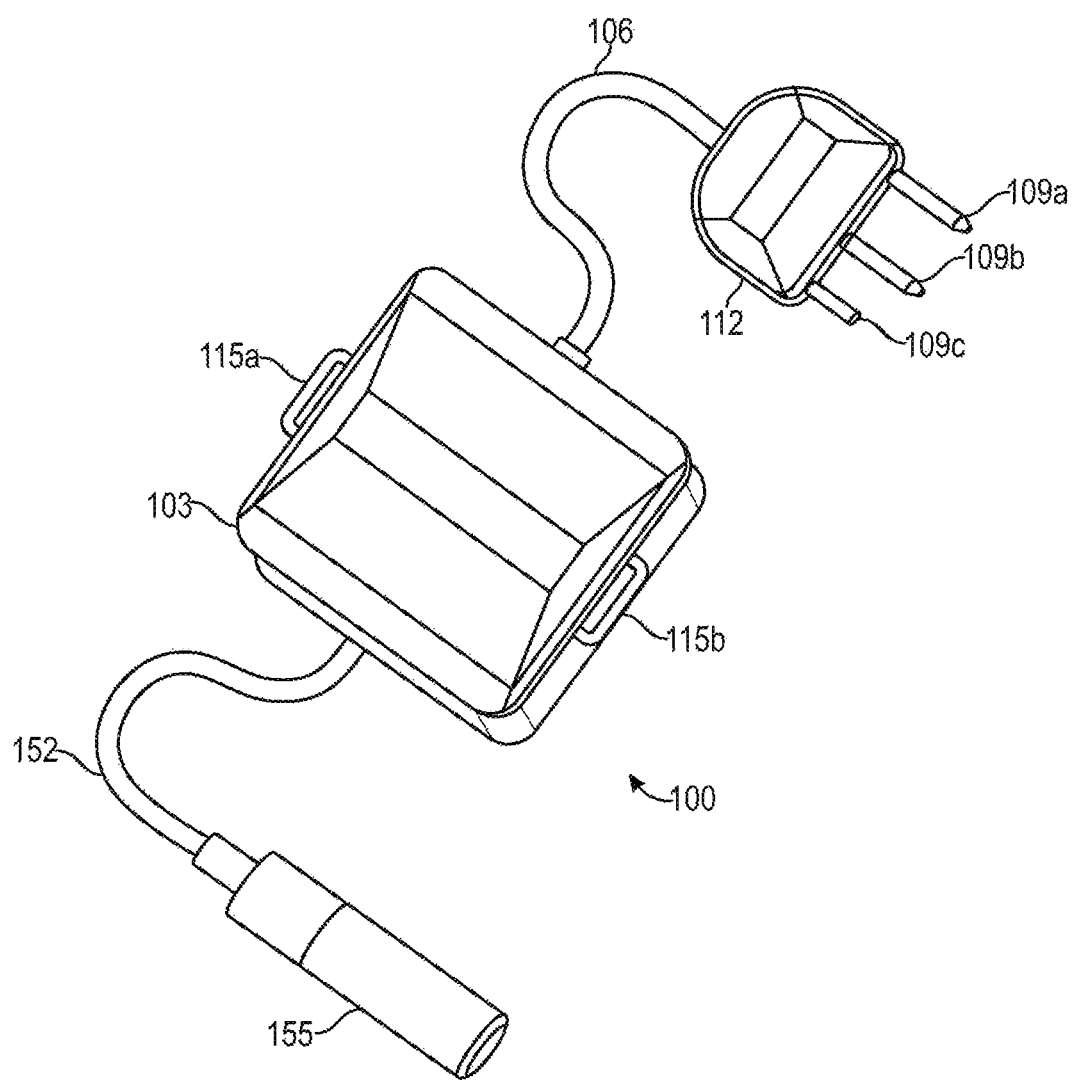
FIG. 2 is another perspective view of the sensor device according to various embodiments of the present disclosure.

Referring now to FIGS. 1 and 2, non-limiting examples of a sensor device 100 are shown in accordance with various embodiments. The sensor device 100 is configured to be embedded in concrete, dirt, or other construction material while still being able to capture measurements of the construction material or properties thereof, and communicate the measurements to a computing device outside of the construction material.

In some embodiments, the sensor device 100 includes an enclosure 103, a wire 106, and one or more probes 109a . . . 109c (collectively "probes 109") extending from and/or partially nested in a probe housing 112, among other features and components as will be described. The enclosure 103 may include an outer surface and a hollow interior, and may further include one or more projections 115a, 115b (collectively "projections 115") defining apertures or openings for insertion of zip-tie and/or wire-tie capability. For instance, the enclosure 103 of the sensor device 100 may be bound to rebar or other desirable location using zip-ties, wire ties, or other suitable connection mechanism via the apertures of the projections, as will be described.

Housed within the enclosure 105 of the sensor device 100 may be circuitry as well as additional components such as, for example, a temperature probe 118, a bulk material electrical resistivity probe 121, a pore solution electrical conductivity probe 124, and/or processing circuitry 127. The processing circuitry 127 may include, for example, a battery 130 or other power source, a microprocessor 133, impedance measurement circuitry 136, temperature measurement circuitry 139, a transceiver 142 (or a transmitter), a power switch 145, memory 148 (e.g., memory of the microprocessor 133 and/or a removable memory card), among other components as may be appreciated.

The impedance measurement circuitry 136 and/or the temperature measurement circuitry 139 may be part of or communicatively coupled to the processing circuitry 127, which includes a microprocessor 133 in various embodiments. The impedance measurement circuitry 136, the temperature measurement circuitry 139, and/or the processing circuitry 127 may be communicatively coupled to the wire 106, which may include an electrically conductive wire extending out of the enclosure 103 to connect to one or more probes 109. The probes 109 may include, for example a pair of electrical resistivity and electrical conductivity probes 109a, 109b and a temperature probe 109c in some embodiments, although other probes 109 may be employed. In some embodiments, the electrical resistivity and electrical conductivity probes 109a, 109b may be gold-coated, although other suitable materials may be employed.

Figure 3:
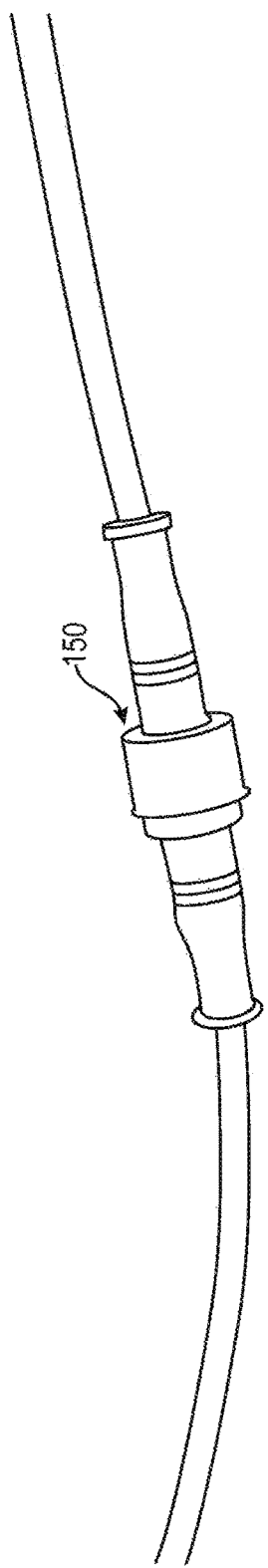
FIG. 3 is a waterproof electrical connector for precast applications according to various embodiments of the present disclosure.
Figure 4C:
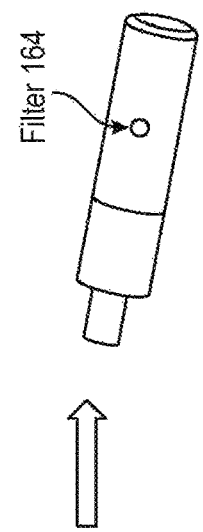
FIG. 4C is a porous plastic filter according to various embodiments of the present disclosure.
Figure 4B:
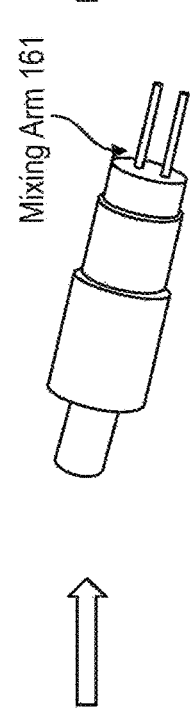
FIG. 4B is a plastic mixing arm according to various embodiments of the present disclosure.
Figure 4A:
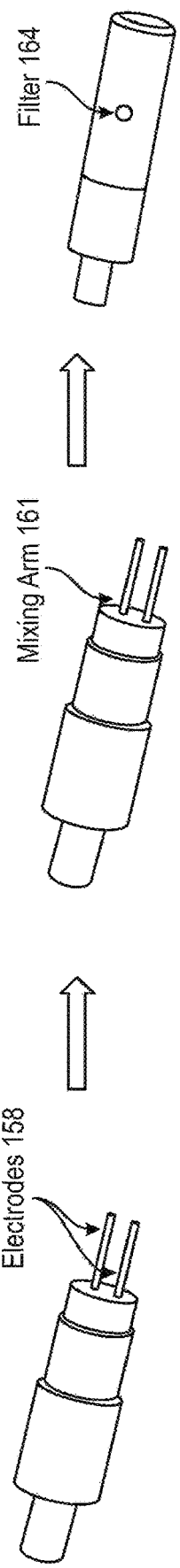
FIG. 4A is a copper electrode according to various embodiments of the present disclosure.

As may be appreciated, the electrical resistivity and electrical conductivity probes 109a, 109b may be used for electrical impedance measurement as they have a standard predetermined geometric factor value (e.g., a K-value) to be utilized for bulk material electrical resistivity and electrical conductivity of pore solution calculations, or other types of calculations. In some embodiments, the temperature and electrical resistivity probes 109a, 109b may be connected using an electrical connector, such as a four pin waterproof electrical connector 150 to the sensor device 100 shown in FIG. 3. This connector may assist in reuse of the sensor device 100. For instance, the connector 150 of FIG. 3 may be used for precast concrete applications with probes 109 that are disposable or reusable, such that the connector 150 is positioned at least partially external to precast concrete. The connector 150 may couple to the wires 106, 152 of FIG. 1 or 2.

While the embodiment of FIG. 1 shows various types of probes 109, additional types of probes may be employed. For instance, in FIG. 2, the sensor device 100 includes not only a first wire 106 that couples the enclosure 103 and the components therein to a first probe arrangement (comprising the probes 109), the sensor device 100 further includes a second wire 152 that couples the housing and the components therein to a second probe arrangement.

In some embodiments, as shown in FIGS. 3A-3C, in order to monitor the electrical conductivity of a pore solution, the second probe arrangement may include electrodes 158 (FIG. 3A), a mixing arm 161 (FIG. 3B) (e.g., a plastic mixing arm 161), and a filter 164 (FIG. 3C) that is connected to the sensor device 100. The electrode 158 may include copper electrodes, the mixing arm 161 may include a plastic mixing arm, and/or the filter 164 may include a porous plastic filter in various embodiments. The filter 164 is not shown in FIGS. 3A and 3B for explanatory purposes. The working of the probes inside the pore solution conductivity relies on the same principles as that of electrical resistivity probe described herein.

Figure 5:
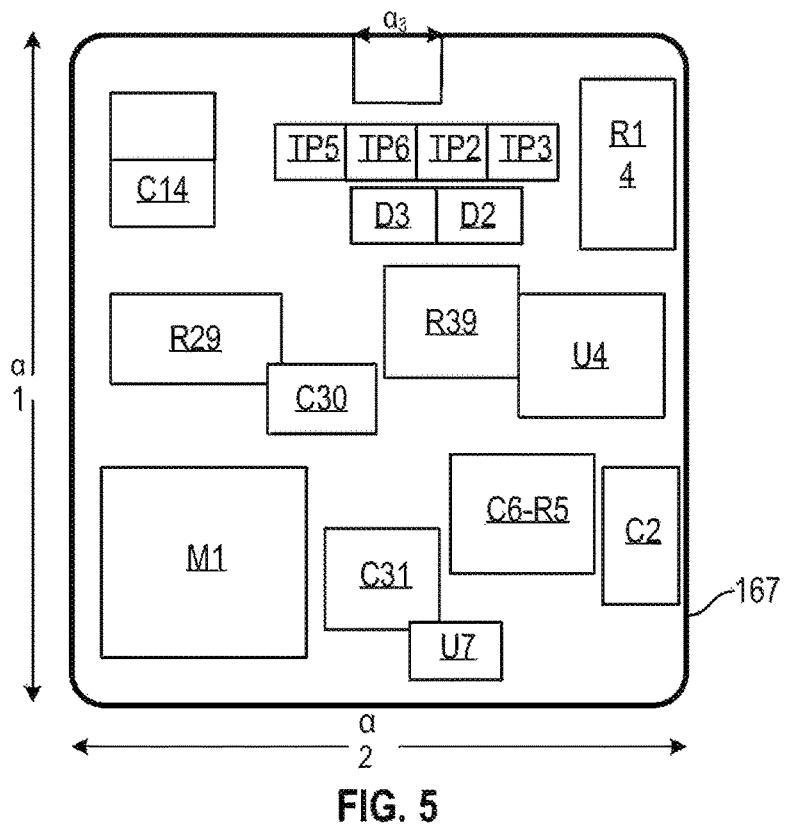
FIG. 5 is an interior layout of a printed circuit board (PCB) and a corresponding components list and description table according to various embodiments of the present disclosure.

Turning now to FIG. 5, FIG. 5 is an interior layout of a printed circuit board (PCB) 167 that may be a part of the processing circuitry 127 is shown according to various embodiments of the present disclosure. In FIG. 5, the PCB 167 includes testpoints TP2, TP3, TP5, TP6, an antenna M1 (e.g., a Bluetooth chip antenna), diodes D2, D3 (e.g., TVS DIODE 5V 12.3V SOD923), capacitor C14 (e.g., CAP CER 10UF 10V X7R 0805), resistor R14 (e.g., RES SMD 100K OHM), resistor R29 (e.g., RES SMD 100K OHM 1%/16 W), capacitor C30 (e.g., CAP CER 01UF 25V X7R 0402), resistor R39 (e.g., RES SMD 47K OHM 1%/16 W), a network analyzer U4 (e.g., IC network analyzer), capacitor C31 (e.g., CAP CER 0.1UF 25V X7R 0402), capacitor-resistor C6-R5 (e.g., CAP CER 01 UF 25V), capacitor C2 (e.g., CAP CER 10PF 10% 25V NPO 0402), and/or other components not described herein. The dimensions of $\alpha_1$ may include 38.00 mm, $\alpha_2$ may include 38.00 mm, and $\alpha_3$ may include 6.00 mm, although other desirable dimensions may be employed.

According to various embodiments described herein, the sensor device 100 and the processing circuitry 127 thereof, and/or an external computing device in communication with the sensor device 100, may be configured to determine initial and final setting times of concrete in a field compared to laboratory calibration; verify water to cement ratio of wet concrete and moisture content of solid concrete; determine in-situ compressive strength of concrete in real-time right from pouring through a twelve month period; make real-time predictions of compressive concrete strength and quality at predefined intervals (e.g., one-day, three-day, seven-day, twenty-eight-day, and fifty-six-day intervals) using electrical resistivity correlation; perform real-time detection of voids or soil contamination in wet concrete during and after the placement of concrete; quantify the properties of concrete, such as permeability, porosity, and diffusion using correlations to electrical resistivity measurements; quantify the pore solution electrical conductivity in concrete during and after placement; perform real-time detection of cracks in concrete structures and trace development over time; perform real-time determination of presence of chloride, sulphate, and/or other ions that affect the integrity and quality of concrete; determine the rate of corrosion of rebar inside the concrete using the absolute value of electrical resistivity of concrete; determine an absolute value of electrical resistivity from electrical impedance measurements and predicting the quality and strength parameters of concrete in real time for up to twelve months or other suitable period of time; perform real-time temperature and alternating current electrical impedance measurements of concrete for a period of up to twelve months or other suitable period of time; transmit or otherwise communicate the absolute value of quality and strength parameters of concrete and the change in parameters over time; perform temperature and alternating current electrical impedance measurement in concrete at a predefined period of time (e.g., twelve months) from a pour of concrete; transmit or otherwise communicate the time, temperature, and electrical impedance measurements to a remote server that processes the electrical impedance data to calculate the value of electrical resistivity of the concrete; determine quality and strength parameters of concrete; and/or transmit or otherwise communicate the quality and strength parameters in real-time to a predetermined enterprise to provide visual interpretation.

Figure 6:
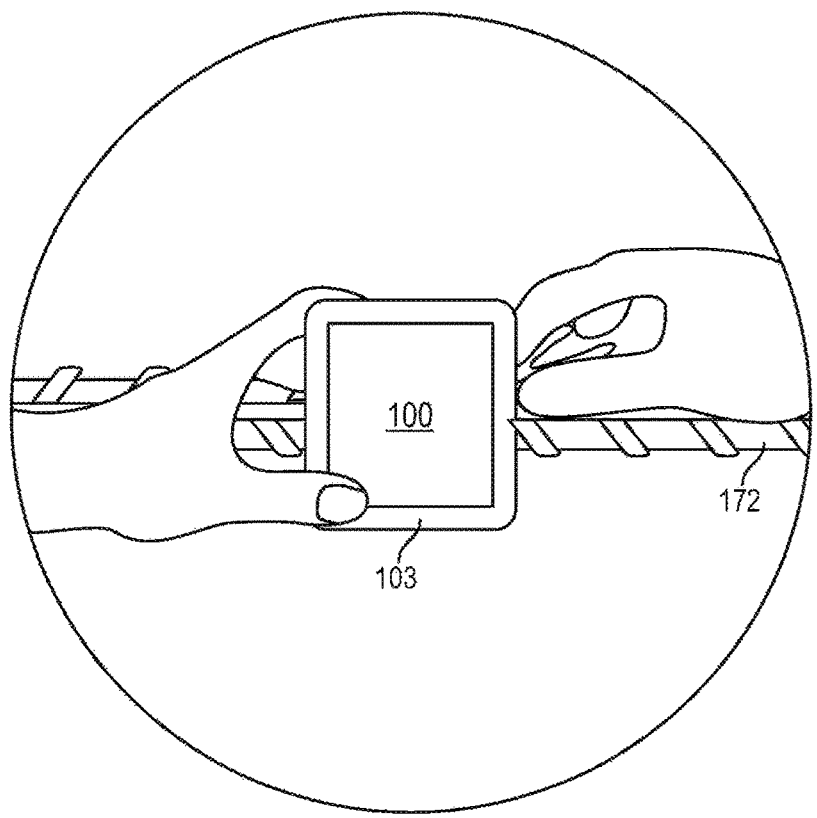
FIG. 6 is an example of an installation process for installing a sensor in concrete formwork according to various embodiments of the present disclosure.
Figure 7:
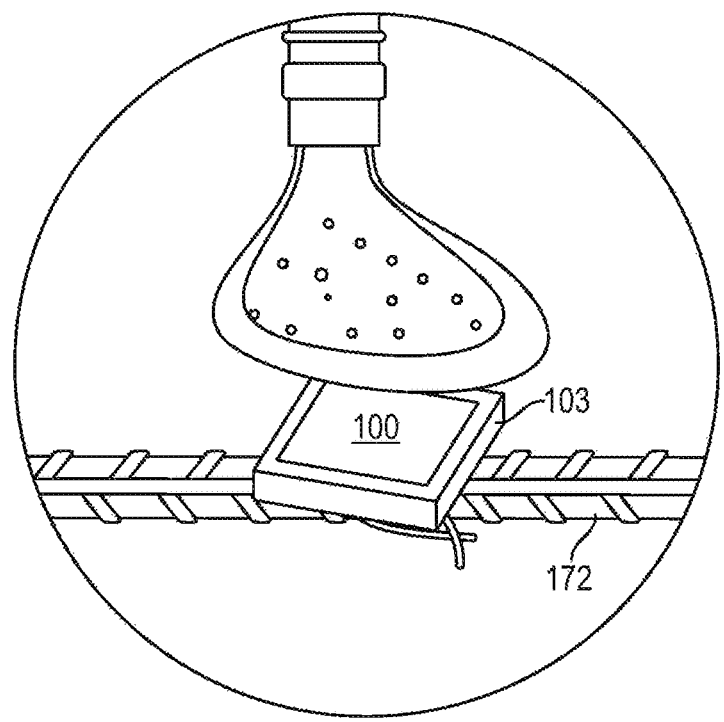
FIG. 7 is an example of pouring concrete after placement of a sensor in concrete formwork according to various embodiments of the present disclosure.
Figure 8:
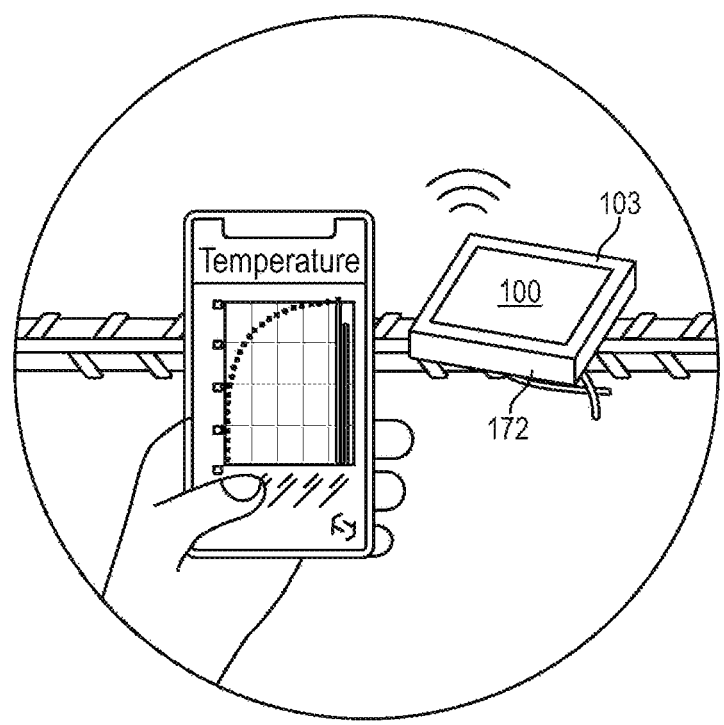
FIG. 8 is an example of communicating wirelessly with a sensor according to various embodiments of the present disclosure.
Figure 9:
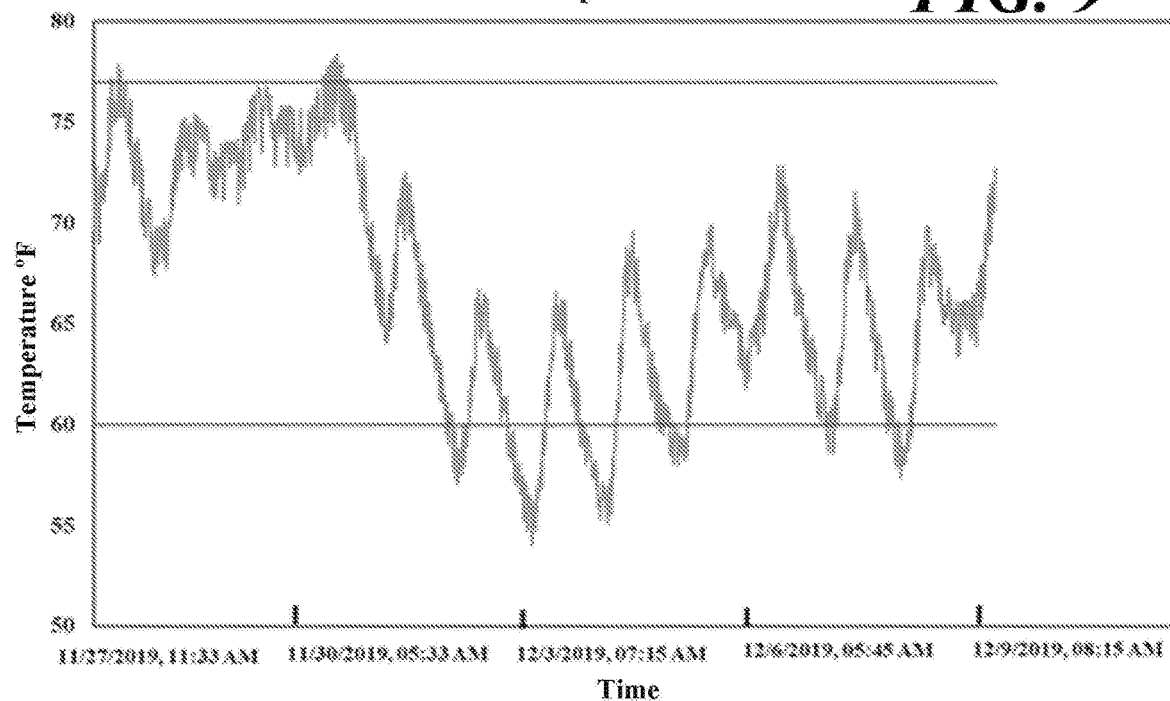
FIG. 9 is a temperature plot showing temperature of concrete versus time according to various embodiments of the present disclosure.
Figure 10:
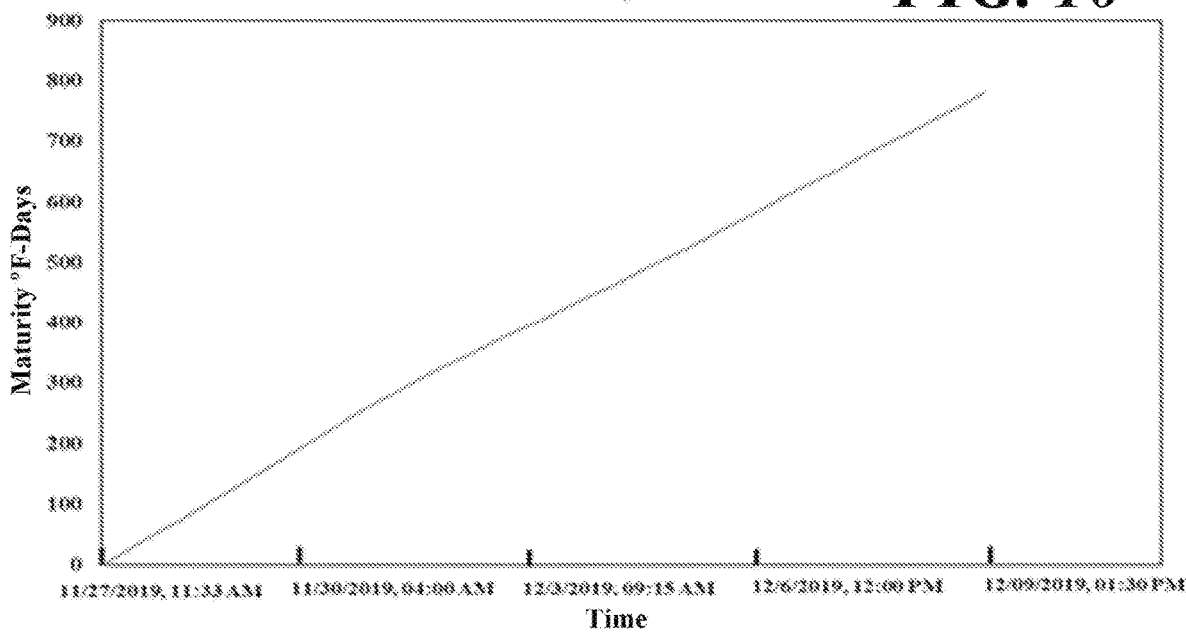
FIG. 10 is a maturity plot showing maturity from temperature versus time according to various embodiments of the present disclosure.
Figure 13:
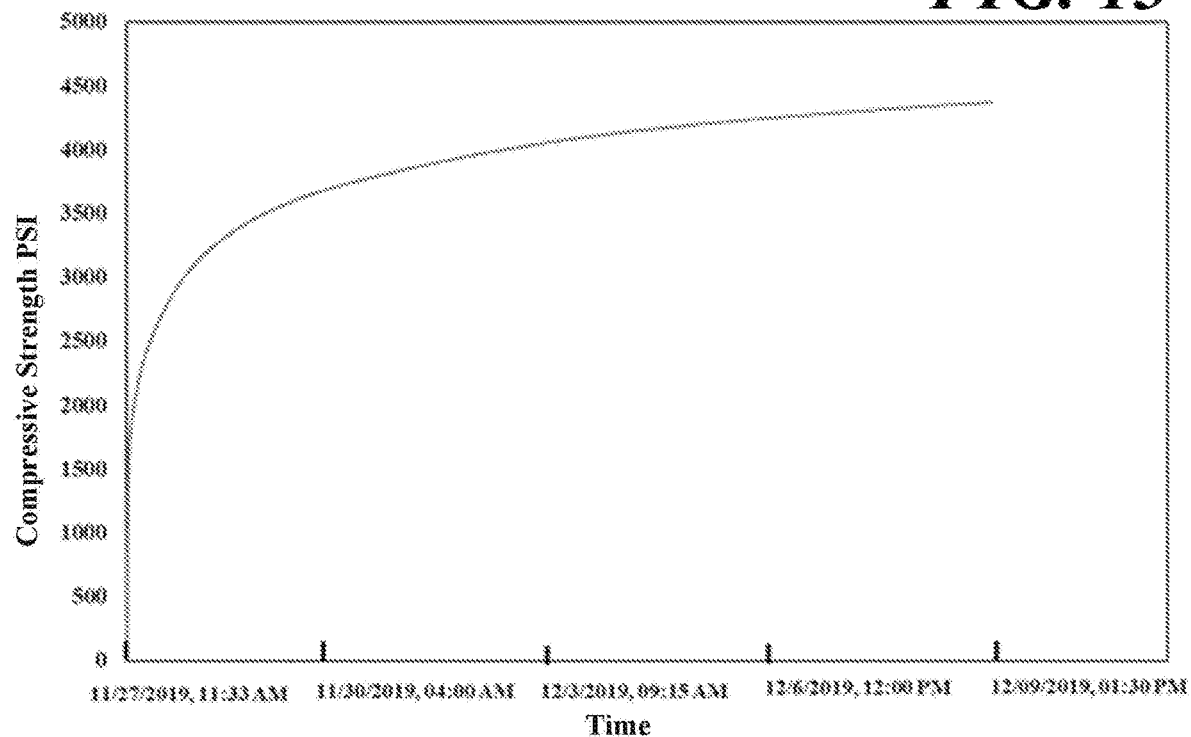
FIG. 13 is a compressive strength using electrical resistivity plot showing compressive strength of concrete versus time according to various embodiments of the present disclosure.

Now, a non-limiting example of a method of use of the above-described sensor is described. First, as shown in FIG. 6, a sensor device 100, as described herein, may be turned on or otherwise enabled and placed onto a concrete reinforcement structure 172, such as rebar. In order to maximize wireless antenna range (e.g., the range of the transceiver 142), the enclosure 103 and the components residing therein (e.g., processing circuitry 127) may be placed at a predefined distance from a surface of the concrete or other material to be poured. In some embodiments, the predefined distance includes approximately three inches (7.5 cm) or other suitable distance.

The sensor device 100 may be tightened or otherwise adequately coupled to the concrete reinforcement structure 172 (e.g., rebar) to reduce the risk of the sensor device 100 being flipped over when the concrete is poured. The transceiver 142 of the sensor device 100 (or other suitable receiver and/or transmitter) may be kept in an upward position to enable a connection and communication between the sensor device 100 and an external computing device, such as a mobile computing device (e.g., a smartphone, laptop, tablet, etc.). In some embodiments, the connection and communication is performed wirelessly although, in alternative embodiments, a third wire (not shown) may be positioned in the concrete such that the third wire projects from a cured surface of the concrete, allowing for a physical connecting between the third wire and one or more computing devices.

Second, before pouring concrete, the wire 110 that connects the enclosure 105 (and the components therein) to the probes 115 may be positioned under the concrete reinforcement structure 172 to protect it from potential damage. Then, it is ensured that temperature and resistivity probes 115 do not touch a ground or any other surface other than the fresh concrete mix. Finally, as shown in FIG. 5, the concrete is poured and cured, while the sensor device 100 starts collecting data which is stored in the memory 148 of the sensor device 100.

After the sensor has been properly installed and fresh concrete poured, a user can connect to the sensor using a computing device 175, for example, to search for nearby sensor devices 100 using a client application. In embodiment in which wireless communication is employed, the computing device 175 may pair with or otherwise connected to the sensor device 100 using the ZigBee® communication protocol, the Bluetooth® communication protocol, or other suitable near field communication protocol.

In some embodiments, the sensor device 100 may transmit data up to forty-nine feet (fifteen meters) of distance between the location of the sensor device 100 and the computing device 175. However, other desirable ranges may be employed. The frequency of the measurements can be adjusted to a desired time interval (e.g., every five minutes), and may have a life of the battery 130 (or a battery life) of six months after installation in some embodiments. It is understood that increasing the time between measurements may increase the life of the battery 130. The sensor device 100 thus may provide real-time data measurements on temperature, maturity, resistivity, and strength of concrete through metrics, graphs, or other data that may be rendered in a user interface to be shown in a display as well as, for example, a point and time when the data was recorded.

The data collected from the sensor device 100 may allow an individual to make more informed decisions during and after the pouring of fresh concrete. For instance, a client application (executable on the computing device 175) may be configured to enable an end user to set thresholds for when the concrete has reached the desired strength, notably, without having to wait three to seven days before getting lab results. Alerts and notifications may inform the user when it is the appropriate time to remove formwork and other building assistance equipment. Over time, all the data collected from the different concrete mix-design and the data collected from the sensor embedded in the fresh concrete could have the potential to provide real-time feedback based on the property of concrete use, job sites geographic location, and concrete curing process.

Figure 14:
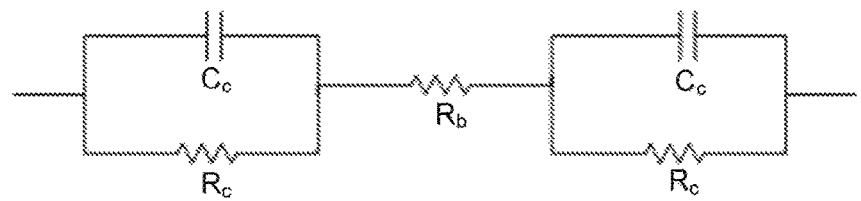
FIG. 14 is an equivalent circuit diagram illustrating a total impedance of a sensor device embedded in concrete or other material according to various embodiments of the present disclosure.

Impedance Model for Electrical Property Characterization: Equivalent Circuit. FIG. 14 depicts a non-limiting example of an equivalent circuit that represents electrical properties of a material (e.g., concrete) to characterize its performance with time. There are many difficulties associated with choosing a correct equivalent circuit. It is derisible, however, to connect the different elements in the circuit to different regions in the impedance data of the corresponding sample. Given the difficulties and uncertainties in establishing this connection, researchers tend to take a pragmatic approach and adopt a circuit which they believe to be most appropriate from their knowledge of the expected behavior of the material under study, and demonstrate that the results are consistent with the circuit used. With the sensor described herein, different possible equivalent circuits were analyzed to find an appropriate equivalent circuit to represent concrete, cementitious materials, and polymers.

Special Bulk Material—Resistance Only. In the equivalent circuit, the electrical contacts were connected in series, and both the electrical contacts were represented using a capacitor $C_c$ and a resistor $R_c$ connected in parallel, as shown in FIG. 12. The bulk material was represented by a resistor $R_b$. In other words, in the equivalent circuit, $R_b$ is the resistance of the bulk material, and $R_c$ and $C_c$ are resistance and capacitance of the contacts, respectively. Both contacts are represented with the same resistance $R_c$ and capacitance $C_c$ in embodiments in which they are made in an identical manner and include identical materials. A total impedance of the equivalent circuit $Z_1$ can be represented as shown in eq. 1 below.

$$Z_1(\sigma) = \frac{R_b(\sigma)}{1+\omega^2 R_b^2 C_b^2} + \frac{2R_c(\sigma)}{1+\omega^2 R_c^2 C_c^2} - j\left\{\frac{2\omega R_c^2 C_c^2(\sigma)}{1+\omega^2 R_c^2 C_c^2} + \frac{2\omega R_b^2 C_b^2(\sigma)}{1+\omega^2 R_b^2 C_b^2}\right\}. \quad (\text{eq. 1})$$

Figure 15:
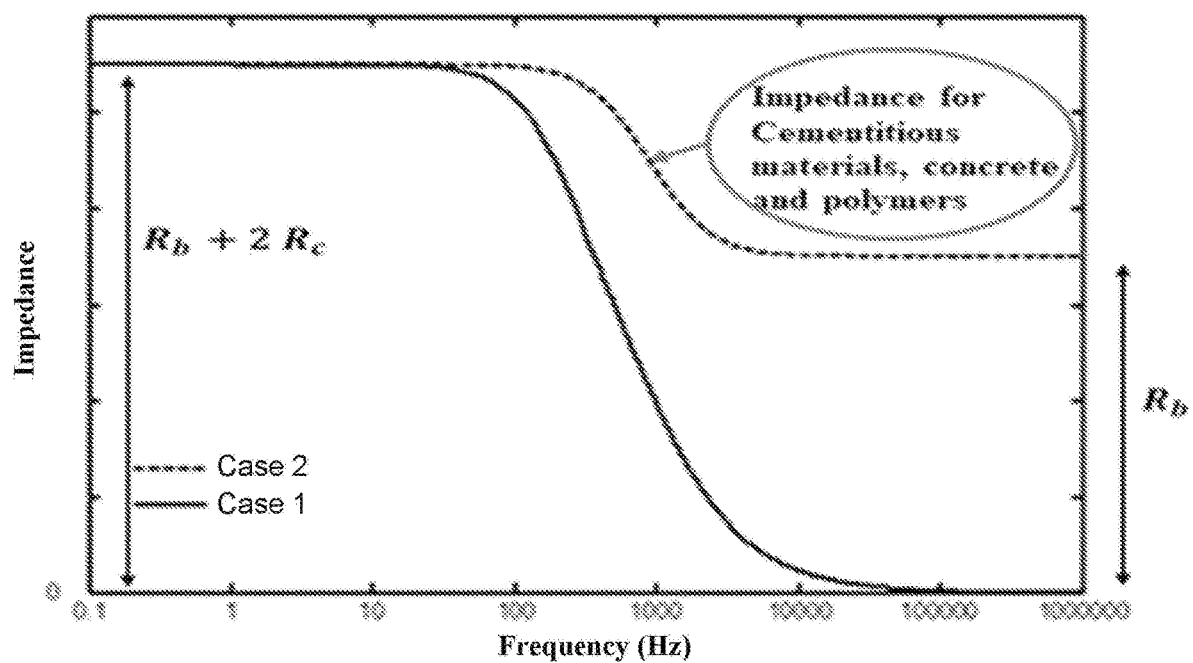
FIG. 15 is a plot of impedance versus frequency of a circuit according to various embodiments of the present disclosure.
Figure 16:
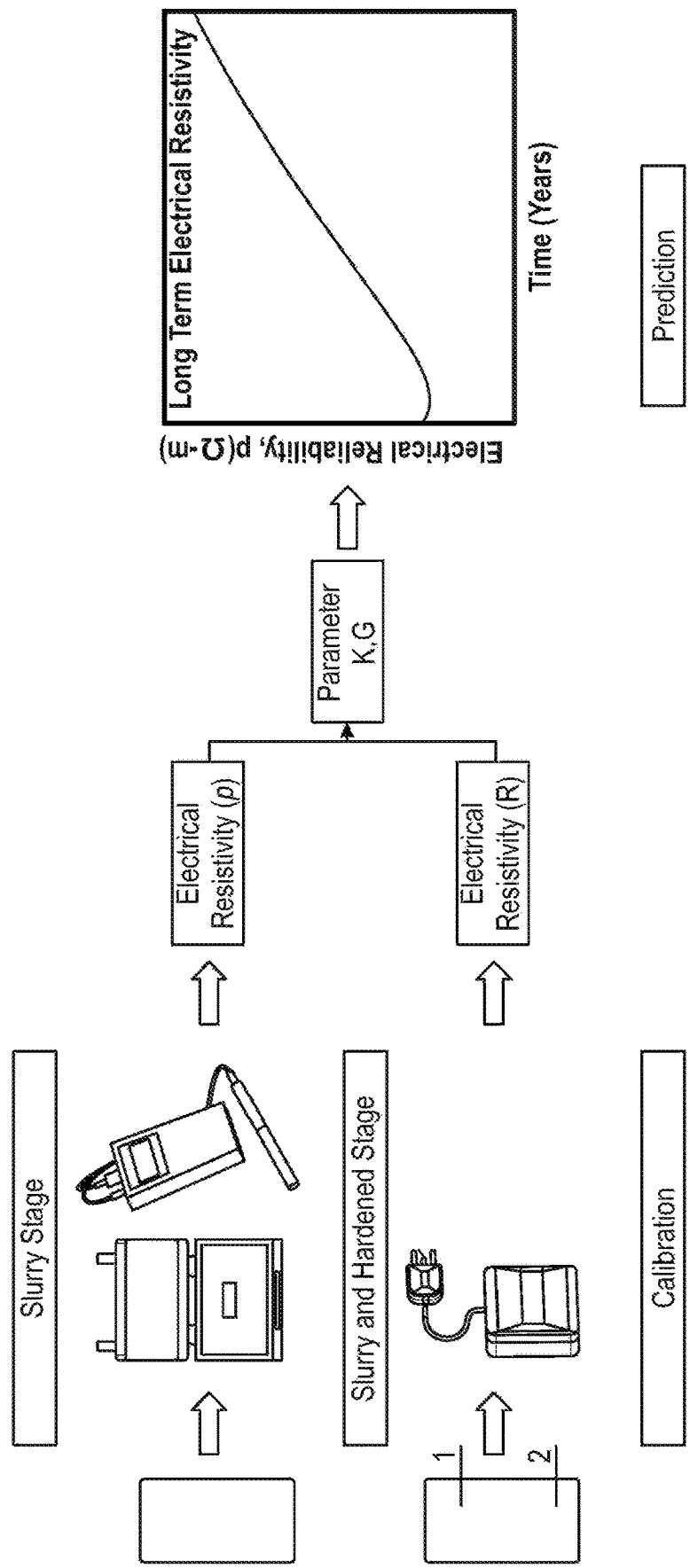
FIG. 16 is a schematic diagram that represents two independent testing parameters that portray a substantially linear relationship between electrical resistance and electrical resistivity.

In this case, the capacitance of the bulk material, denoted $C_b$, is assumed to be negligible, as can be seen in FIG. 15. When the frequency of the applied signal is very low, $\omega \to 0$, $Z_2 = R_b + 2R_c$, and when it is very high, $\omega \to \infty$, $Z_2 = R_b$. The shape of the curves shown in the figure is very much influenced by material response and the two probe instruments used for monitoring. Testing of concrete indicated that electrical impedance represented their behavior and hence the bulk material properties can be represented by resistivity and characterized at a frequency of 100 kHz to 1 MHz using the two probes. The electrical resistance of material can be obtained by measuring impedance at high AC frequencies and can be converted into electrical resistivity using K-value as shown below.

Figure 17:
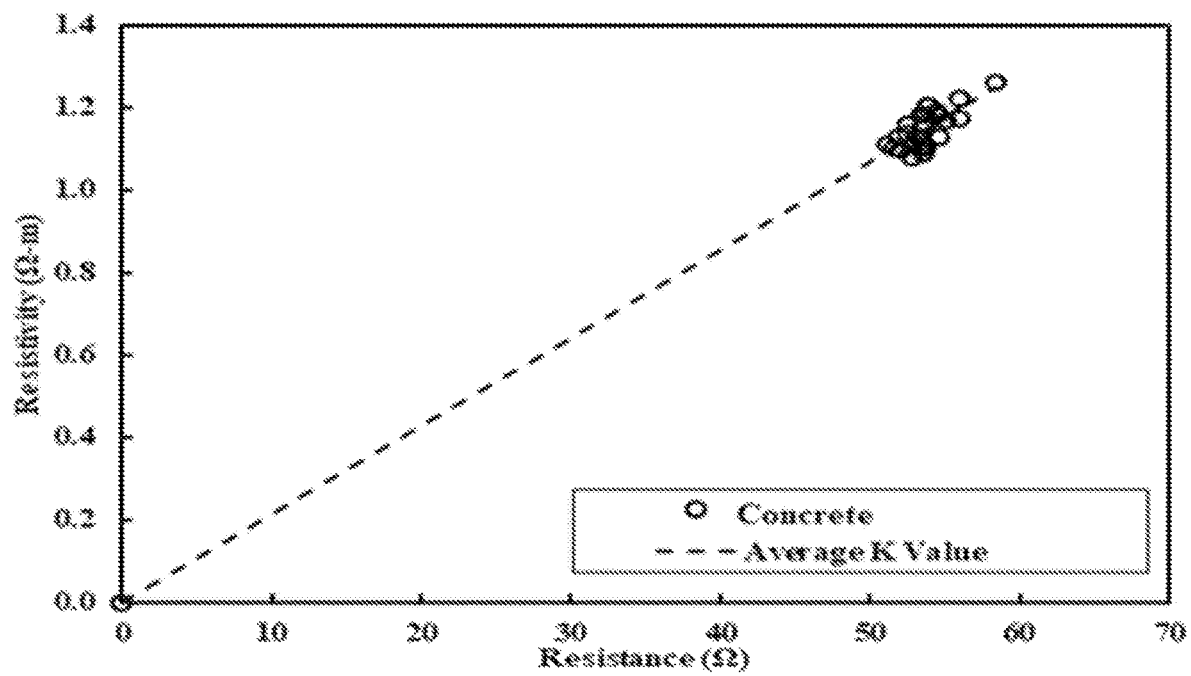
FIG. 17 is a plot illustrating a linear relationship between electrical resistance and electrical resistivity according to various embodiments of the present disclosure.
Figure 18:
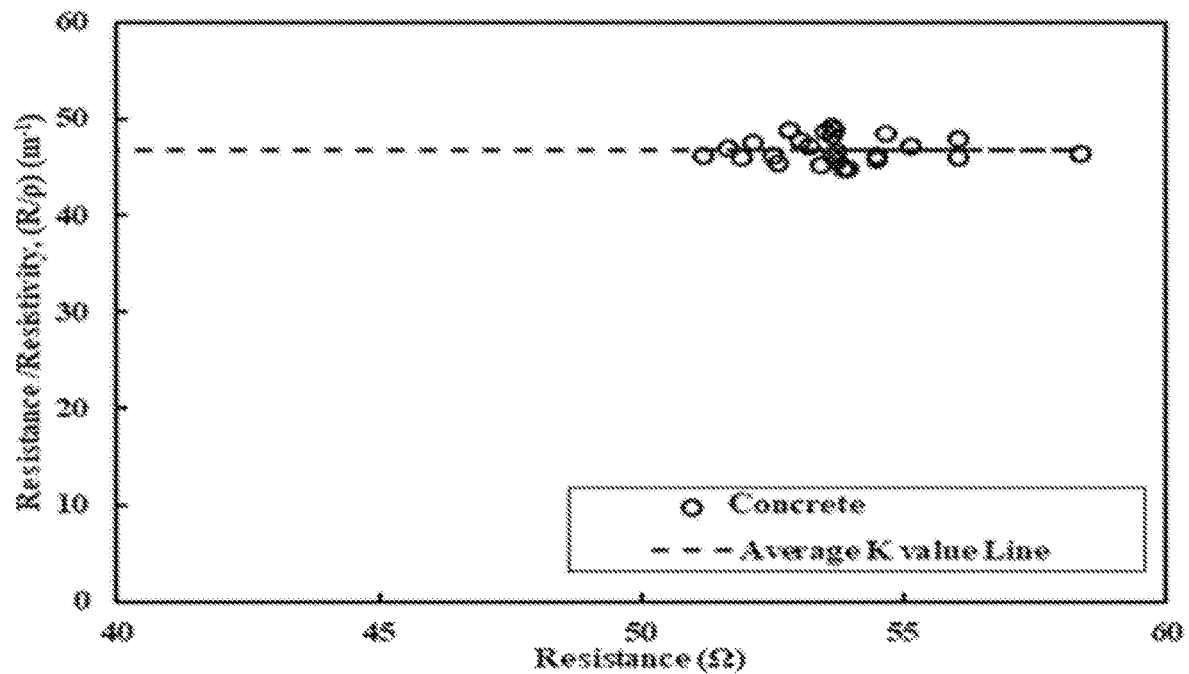
FIG. 18 is a plot of electrical resistance versus electrical resistivity for concrete according to various embodiments of the present disclosure.

The relation between electrical resistance, electrical resistivity and K-value is given by eq. 1 below:

$$\rho = \frac{R}{K+GR}, \quad (\text{eq. 2})$$

where the constants K and G are constants. FIG. 17 further shows that electrical resistance and electrical resistivity have a linear relationship for concrete.

Figure 19:
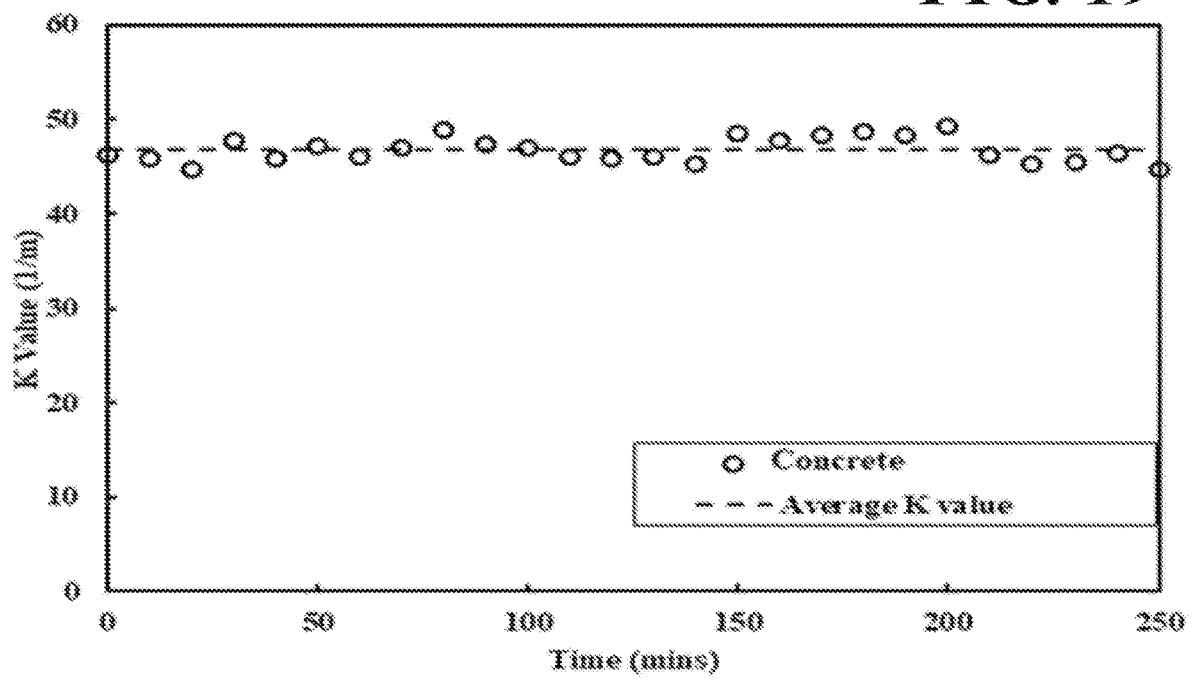
FIG. 19 is a plot of a K-value for concrete versus time according to various embodiments of the present disclosure.

K-value Characterization. The electrical resistance R of the concrete was measured using the sensor described herein and the electrical resistivity $\rho$ of the concrete was measured using both digital resistivity meter and conductivity meter for initial curing period to calculate the K-value at room temperature. The average K-value for cementitious materials for the prescribed sensor is developed during the initial curing period, as shown in FIG. 19.

The electrical impedance of concrete at certain ranges of frequency correlates to material property, electrical resistivity of concrete. Therefore, according to various embodiments, the electrical properties have been well correlated with important early-stage properties of concrete such that a variety of properties may be established including water cement ratio, insitu compressive strength, initial and final setting times, transport property detection, pore solution electrical conductivity, hydration of cementitious materials and damage detection.

Determination of Water to Cement Ratio of Concrete. The measurement of water to cement ratio of concrete before or during pouring the concrete is important in the construction industry to ensure the appropriate quality of the concrete delivered by concrete trucks to the construction site. Every concrete mix design has a specified water to cement ratio. The water to cement ratio has an impact on the performance of concrete, its hydration, and porosity. Higher water content increases the porosity of the hardened concrete and thus, decreases its strength and durability. It is important to monitor the water/cement ratio in real-time. Accordingly, the sensor device 100 described herein helps avoiding pouring low-strength or low-quality concrete, the replacement of which will be very costly and, in some cases, impossible.

Figure 20:
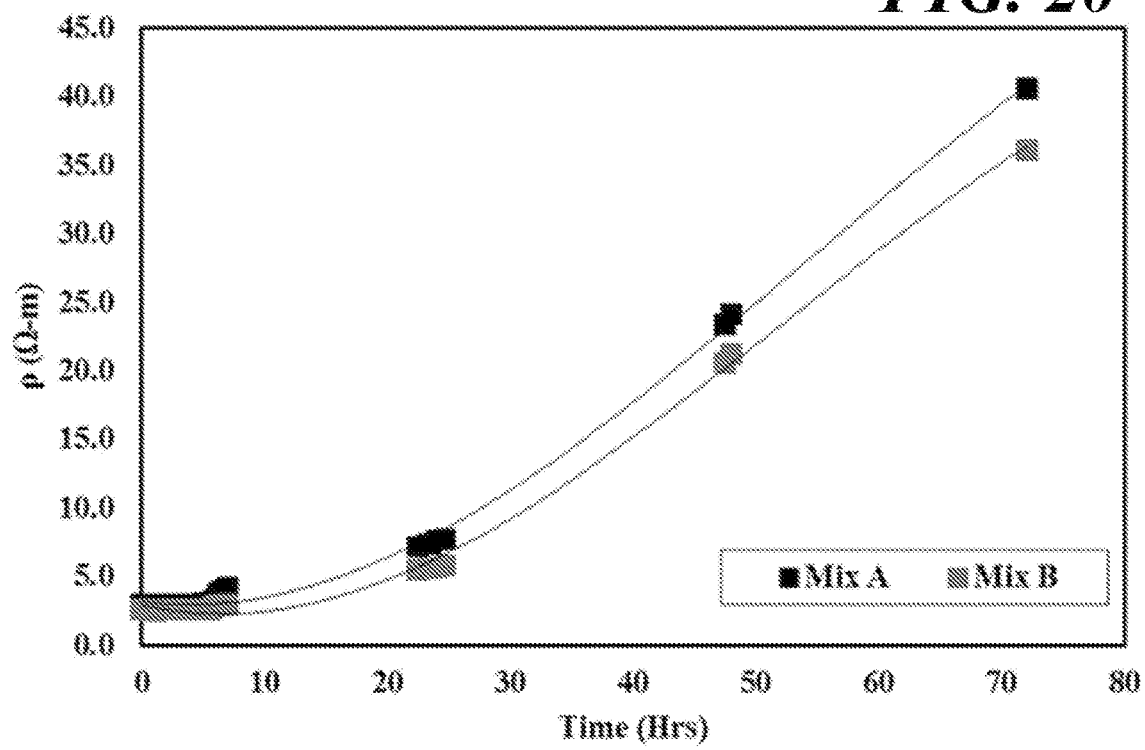
FIG. 20 is a plot showing a resistivity versus time curve according to various embodiments of the present disclosure.
Figure 21:
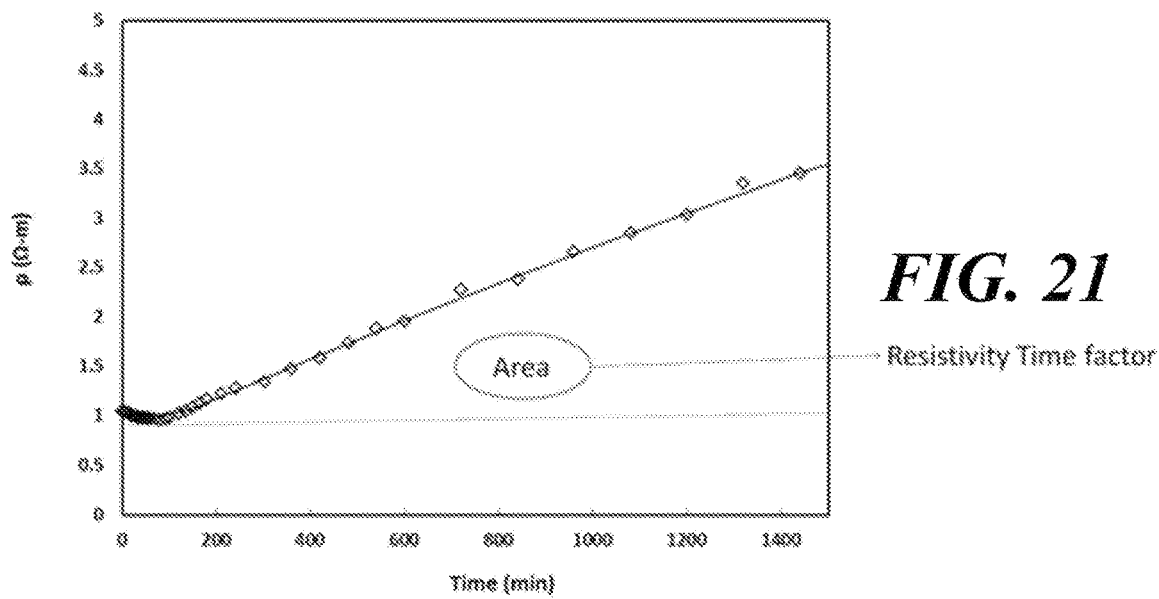
FIG. 21 is a plot showing a resistivity time factor according to various embodiments of the present disclosure.

Findings. The electrical resistivity of the concrete slurry was found to vary between 2.5 to 3 $\Omega$-m based on the water content added. For Mix A, the resistivity was 2.9 $\Omega$-m, for Mix B it was 2.60 $\Omega$-m, due to increased water to binder ration, as shown in FIG. 20. The resistivity of the flyash concrete varied between 36.13 to 40.5 for percentages Mixes A and B after three days of curing. It was also observed that the resistivity of flyash concrete were lower for higher water to binder ratio. For Mix A, the resistivity time factor was 51.7 $\Omega$-m-day and compressive strength was 9.1 MPa after one day of curing. The resistivity time factor was 354.8 $\Omega$-m-day and 17.2 MPa after two days of curing. After three days of curing, the resistivity time factor was 1061.8 MPa and compressive strength of 21 MPa. Accordingly, it is evident that the water cement ratio impact shows correlation to electrical resistivity measurements during initial placement of concrete. Such electrical measurements made in the field provide indication of quality of cementitious materials without requiring additional testing.

Prediction of In-Situ Compressive Strength of Concrete after Pouring. Assessment of the compressive strength of concrete during the first few days from pouring up to sever days after pouring is important for the optimization of formwork removal, post tensioning, and opening of roadways especially in the winter. The rate of hydration of every concrete mix design differs due to various factors of influence. The electrical resistivity of concrete over time can be used to estimate the compressive strength of concrete, rate of hydration, and calculation of percentage of strength gain.

Long term strength prediction may further be employed. Specifically, established resistivity time factor (RTF) versus strength correlation may be employed to predict the long-term compressive strength of concrete. A depiction of the results is presented below.

Figure 22:
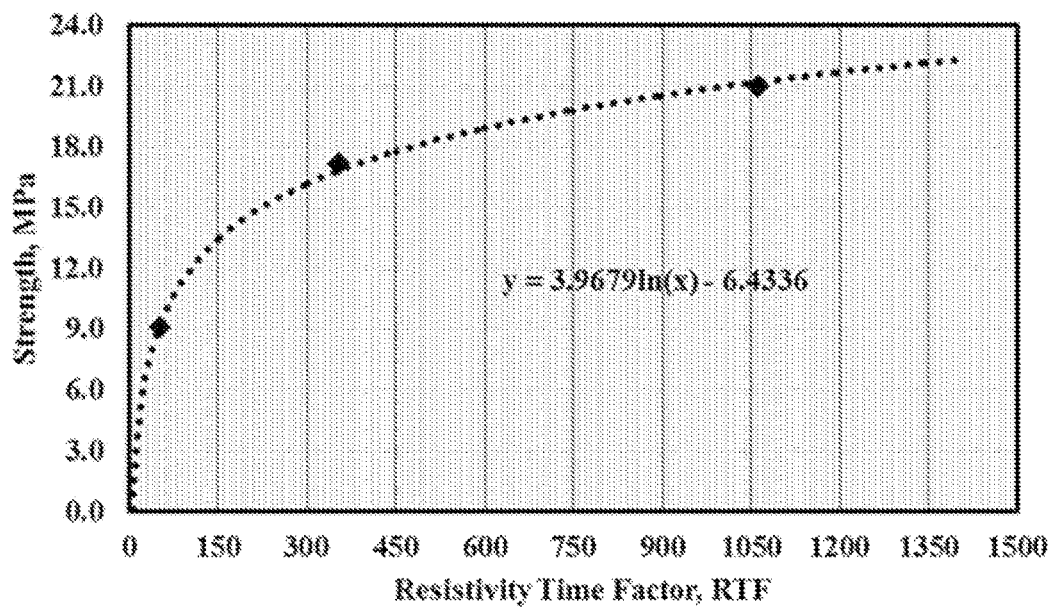
FIG. 22 is a table showing a cumulative resistivity time factor versus compressive strength according to various embodiments of the present disclosure.

One-Day Results. The RTF Factor for one day was 33.7 $\Omega$-m-day. Using a prediction curve, the compressive strength was 7±0.5 MPa. The actual one-day strength obtained by performing compressive strength was 7.03 MPa, as shown in FIG. 22.

Two-Days Results. The RTF Factor for two days was 286.2 $\Omega$-m-day. Using a prediction curve, the compressive strength was 15.4±0.5 MPa. The actual two-day strength obtained by performing compressive strength was 15.3 MPa.

Three-Days Results. The RTF Factor for 3 days was 913.3 $\Omega$-m-day. Using a prediction curve, the compressive strength was 19.5±0.5 MPa. The actual one-day strength obtained by performing compressive strength was 19.1 MPa. The prediction of compressive strength using resistivity time factor curve was accurate up to about ±0.5 MPa. Accordingly, it is evident that the compressive strength shows linear correlation to electrical resistivity and resistivity time factor (RTF) may be utilized for prediction of compressive strength without need for break tests.

Initial and Final Setting of Concrete (ASTM C403). Currently, the determination of initial and final setting time concrete is performed using Vicat Apparatus ASTM C403: "Standard Test Method for Time of Setting of Concrete Mixtures by Penetration Resistance." This laboratory procedure is labor intensive and cannot be employed in the field. Setting times are important for deciding on the surface finishing of concrete and for other sequence of operations in the construction. Monitoring the absolute value of electrical resistivity of concrete enables identification of different stages of hydration reaction inside concrete leading to correlation to setting time of concrete. Accordingly, electrical impedance measurements present a non-invasive, in-site process for detection of setting time of concrete.

Assessment of Transport properties of Concrete. Two important electrical parameters required for reliable and accurate assessment of the microstructural properties of concrete are electrical conductivity of bulk concrete and its pore solution. The measurement of these two properties also enables calculation of formation factor for concrete materials over time. One of the major drawbacks of current available techniques is the inability to monitor these electrical properties of concrete materials on the field and in real time for long term. The measurement of bulk electrical conductivity of concrete has been demonstrated. Monitoring the electrical conductivity in real time enables determination of transport properties of concrete. Accordingly, this assessment can substitute Standards such as ASTM C1202: "Standard Test Method for Electrical Indication of Concrete's Ability to Resist Chloride Ion Penetration" and ASTM C1543: "Standard Test Method for Determining the Penetration of Chloride Ion into Concrete by Ponding."

Within the embodiments of the invention described, the electrical and temperature measurements may be made using disposable and/or reusable probes connected to sensor via a 4 pin waterproof electrical connector. For example, a disposable sensor may exploit Bluetooth connectivity for short range low power communications and ad-hoc, LORA or other network protocols to communicate electrical measurement data to a node or nodes wherein it is pushed to remote servers, what is commonly referred to today as "the cloud", through one or more different network interfaces and/or network protocols. Subsequently, this cloud stored data can be analyzed in real time and/or periodically to determine one or more of the measurements described.

In addition to measuring, for example, temperature, AC electrical resistivity, and AC electrical conductivity of pore solution, it would be evident that additional parameters as discussed and described in respect of embodiments of the invention may be measured and monitored, including, but not limited to, concrete moisture content, concrete internal relative humidity, concrete pH, concrete mixture consistency, concrete workability (slump), and concrete air content.

Accordingly, based on the foregoing, a method for performing real-time concrete monitoring is described that includes providing at least one sensor device 100 (e.g., one or more of the sensor device 100 described above). The sensor device 100 includes an enclosure 103 configured to couple the sensor to a concrete reinforcing structure 172, the enclosure comprising a temperature probe 118, impedance measurement circuitry 136, temperature measurement circuitry 139, and a transceiver 142. The sensor device 100 further includes a first electrical conducting wire 106 (or "first wire 106") extending out from the enclosure 103 being electrically and/or communicatively connected to at least one probe 109. The processing circuitry 127 may be configured to perform at least one impedance measurement using the at least one probe 109 and a temperature measurement using the temperature probe 109c; and communicate at least one of the at least one impedance measurement, the at least one temperature measurement, and derivative information associated therewith, to a computing device 175 via the transceiver 142. The method further includes affixing the enclosure 103 of the at least one sensor device 100 to the concrete reinforcing structure 172; pouring concrete or other material in an area such that the at least one sensor device 100 is wholly or partially encapsulated in the concrete such that the at least one probe 109 is in contact with the concrete; receiving, by at least one computing device 175, at least one of the at least one impedance measurement, the at least one temperature measurement, and derivative information associated therewith from the at least one sensor device 100; determining, by the at least one computing device 175, at least one of a temperature, a maturity, a resistivity, and a strength of the concrete based on at least one of: the at least one impedance measurement, the at least one temperature measurement, and derivative information associated therewith; and displaying, by the at least one computing device 175, information associated with at least one of the temperature, the maturity, the resistivity, and the strength of the concrete in a display device.

Additionally, a method is described that includes performing an AC electrical impedance measurement using a sensor device 100 positioned inside a material comprising at least one of: concrete, cementitious material, liquid, soil, polymer, and a combination thereof in real-time; and determining a characteristic of the material based upon at least the electrical impedance measurement, wherein determining the characteristic of the material further comprises adjusting the AC electrical impedance measurement based at least in part on an appropriate electrical circuit, geometric factor, and temperature.

In some embodiments, the material includes concrete in one of a wet and a hardened state, and the characteristic of the material is at least one of the following: a water to cement ratio of the concrete; an estimated in-situ compressive strength of the concrete after pouring; at least one of seven-day, twenty-eight-day, and fifty-six-day compressive strength of the concrete; at least one of the initial and final setting time of the concrete; a transport property of the concrete (e.g., permeability, diffusivity, porosity, and any combination thereof); a presence of voids inside the concrete; a presence of a crack within the concrete; and pore solution characteristics.

The electrical impedance may be obtained using an equivalent circuit, as shown in FIG. 14, and a dependence of geometric factor determined to obtain at least one of electrical resistivity and electrical conductivity to determine the characteristic, where the characteristic may include a water to cement ratio of the concrete; an in-situ compressive strength of the concrete after pouring; a prediction of at least one of seven-day, twenty-eight-day, and fifty-six-day compressive strength of the concrete; a detection of at least one of the initial and final setting time of the concrete; and an assessment of a transport property of the concrete selected from a group consisting of permeability, diffusivity, and porosity.

The features, structures, or characteristics described above may be combined in one or more embodiments in any suitable manner, and the features discussed in the various embodiments are interchangeable, if possible. In the following description, numerous specific details are provided in order to fully understand the embodiments of the present disclosure. However, a person skilled in the art will appreciate that the technical solution of the present disclosure may be practiced without one or more of the specific details, or other methods, components, materials, and the like may be employed. In other instances, well-known structures, materials, or operations are not shown or described in detail to avoid obscuring aspects of the present disclosure.

Although the relative terms such as "on," "below," "upper," and "lower" are used in the specification to describe the relative relationship of one component to another component, these terms are used in this specification for convenience only, for example, as a direction in an example shown in the drawings. It should be understood that if the device is turned upside down, the "upper" component described above will become a "lower" component. When a structure is "on" another structure, it is possible that the structure is integrally formed on another structure, or that the structure is "directly" disposed on another structure, or that the structure is "indirectly" disposed on the other structure through other structures.

In this specification, the terms such as "a," "an," "the," and "said" are used to indicate the presence of one or more elements and components. The terms "comprise," "include," "have," "contain," and their variants are used to be open ended, and are meant to include additional elements, components, etc., in addition to the listed elements, components, etc. unless otherwise specified in the appended claims. The terms "first," "second," etc. are used only as labels, rather than a limitation for a number of the objects.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A sensor device configured to be embedded within concrete and monitor the concrete when embedded therein, comprising:
   a first probe arrangement comprising a plurality of probes configured to measure electrical resistivity, electrical conductivity, and temperature;
   an enclosure comprising a bulk material electrical resistivity probe, a pore solution electrical conductivity probe, and a temperature probe, wherein the enclosure further comprises a battery, processing circuitry, a transceiver, impedance measurement circuitry, and temperature measurement circuitry;
   wherein the processing circuitry is configured to: generate, using the plurality of probes, an impedance measurement, an electrical conductivity measurement, and a temperature measurement associated with the concrete, and the impedance measurement is determined by measuring impedance of the concrete at a frequency between 100 kHz to 1 MHz and converting the impedance measurement to the electrical resistivity using a predetermined geometric factor value (K-value);
   wherein the processing circuitry is further configured to communicate at least one of: the impedance measurement, the electrical conductivity measurement, the temperature measurement, and derivative information associated therewith, to a computing device external to the concrete via the transceiver in real-time; and
   a connection device configured to couple the enclosure to a concrete reinforcing structure within the concrete such that the plurality of probes of the probe arrangement are in electrical contact with the concrete;
   wherein the sensor device comprises a second probe arrangement, the second probe arrangement comprising a plurality of electrodes, a mixing arm, and a filter.

2. The sensor device according to claim 1, wherein the sensor device is at least partially disposable or reusable.

3. The sensor device according to claim 2, wherein the plurality of probes of the first probe arrangement are each disposable or reusable.

4. The sensor device according to claim 1, wherein the sensor device is embedded in the concrete, and the concrete reinforcing structure comprises rebar.

5. The sensor device according to claim 1, wherein: the impedance measurement is generated by the processing circuitry; and
   at least one of the processing circuitry and a client application executing on the computing device external to the concrete is configured to determine the electrical resistivity of the concrete based at least in part on the impedance measurement.

6. The sensor device according to claim 1, further comprising a wire that couples the processing circuitry to the first probe arrangement.

7. The sensor device according to claim 1, wherein at least one of the processing circuitry and a client application executing on the computing device external to the concrete is configured to perform at least two of:
   determining initial and final setting times of the concrete as compared to laboratory calibration;
   verifying water to cement ratio of wet concrete and moisture content of solid concrete;
   determining in-situ compressive strength of concrete in real-time from pouring through a predetermined time period;
   generating real-time predictions of compressive concrete strength and quality at predefined intervals using electrical resistivity correlation; and
   performing real-time detection of voids or soil contamination in wet concrete during and after placement of the concrete.

8. The sensor device according to claim 1, wherein at least one of the processing circuitry and a client application executing on the computing device external to the concrete is configured to perform at least one of:
   quantifying a property of the concrete using a correlation to electrical resistivity measurements, wherein the property is one of permeability, porosity, and diffusion;
   quantifying pore solution electrical conductivity of the concrete during and after placement;
   performing real-time detection of cracks in the concrete and trace development over time;
   performing real-time determination of presence of at least one of chloride and sulphate that affect integrity and quality of the concrete; and
   determining a rate of corrosion of rebar inside the concrete using an absolute value of electrical resistivity of concrete.

9. The sensor device according to claim 1, wherein at least one of the processing circuitry and a client application executing on the computing device external to the concrete is configured to perform at least two of:
   determining an absolute value of electrical resistivity from electrical impedance measurements and predicting quality and strength parameters of the concrete in real time for a predetermined period of time;
   performing real-time temperature and alternating current electrical impedance measurements of the concrete for a predetermined period of time;
   transmitting an absolute value of quality and strength parameters of the concrete and a change in parameters over time;

performing temperature and alternating current electrical impedance measurements of the concrete at a predefined period of time from a pour of concrete;

transmitting a time, a temperature, and an electrical impedance data to a remote server that processes the electrical impedance data to calculate a value of electrical resistivity of the concrete; and transmitting quality and strength parameters of the concrete in real-time to the computing device to provide visual interpretation.

10. A method for monitoring concrete, comprising:

providing a sensor device, wherein the sensor device comprises: a first probe arrangement comprising a plurality of probes; an enclosure comprising a bulk material electrical resistivity probe, a pore solution electrical conductivity probe, and a temperature probe, wherein the enclosure further comprises a battery, processing circuitry, a transceiver, impedance measurement circuitry, and temperature measurement circuitry; and a second probe arrangement, the second probe arrangement comprising a plurality of electrodes, a mixing arm, and a filter;

coupling the enclosure of the sensor device, using a connection device, to a concrete reinforcing structure such that the plurality of probes of the probe arrangement are in electrical contact with the concrete when poured;

generating, using the plurality of probes, an impedance measurement, an electrical conductivity measurement, and a temperature measurement associated with the concrete, wherein the impedance measurement is determined by measuring impedance of the concrete at a frequency between 100 kHz to 1 MHz and converting the impedance measurement to the electrical resistivity using a predetermined geometric factor value (K-value); and communicating at least one of the impedance measurement, the electrical conductivity measurement, the temperature measurement, and derivative information associated therewith, to a computing device external to the concrete via the transceiver in real-time.

11. The method according to claim 10, wherein the sensor device is at least partially disposable or reusable.

12. The method according to claim 11, wherein the plurality of probes of the first probe arrangement are each disposable or reusable.

13. The method according to claim 10, further comprising embedding the sensor device in the concrete, wherein the concrete reinforcing structure comprises rebar.

14. The method according to claim 10, wherein:

the impedance measurement is generated by the processing circuitry; and the method further comprises determining, using at least one of the processing circuitry and a client application executing on the computing device external to the concrete, the electrical resistivity of the concrete based at least in part on the impedance measurement.

15. The method according to claim 10, further comprising providing a wire that couples the processing circuitry to the probe arrangement.

16. The method according to claim 10, further comprising performing, using at least one of the processing circuitry and a client application executing on the computing device external to the concrete, at least two of:

determining initial and final setting times of the concrete as compared to laboratory calibration;

verifying water to cement ratio of wet concrete and moisture content of solid concrete;

determining in-situ compressive strength of concrete in real-time from pouring through a predetermined time period;

generating real-time predictions of compressive concrete strength and quality at predefined intervals using electrical resistivity correlation; and performing real-time detection of voids or soil contamination in wet concrete during and after placement of the concrete.

17. The method according to claim 10, further comprising performing, using at least one of the processing circuitry and a client application executing on the computing device external to the concrete, at least one of quantifying a property of the concrete using a correlation to electrical resistivity measurements, wherein the property is one of permeability, porosity, and diffusion;

quantifying pore solution electrical conductivity of the concrete during and after placement;

performing real-time detection of cracks in the concrete and trace development over time;

performing real-time determination of presence of at least one of chloride and sulphate that affect integrity and quality of the concrete; and determining a rate of corrosion of rebar inside the concrete using an absolute value of electrical resistivity of concrete.

18. The method according to claim 10, further comprising performing, using at least one of the processing circuitry and a client application executing on the computing device external to the concrete, at least two of:

determining an absolute value of electrical resistivity from electrical impedance measurements and predicting quality and strength parameters of the concrete in real time for a predetermined period of time;

performing real-time temperature and alternating current electrical impedance measurements of the concrete for a predetermined period of time;

transmitting an absolute value of quality and strength parameters of the concrete and a change in parameters over time;

performing temperature and alternating current electrical impedance measurements of the concrete at a predefined period of time from a pour of concrete;

transmitting a time, a temperature, and an electrical impedance data to a remote server that processes the electrical impedance data to calculate a value of electrical resistivity of the concrete; and transmitting quality and strength parameters of the concrete in real-time to the computing device to provide visual interpretation.

\* \* \* \* \*